US008317705B2

(12) United States Patent
Stapf et al.

(10) Patent No.: US 8,317,705 B2
(45) Date of Patent: Nov. 27, 2012

(54) METHOD FOR GENERATING A MOTION-CORRECTED 3D IMAGE OF A CYCLICALLY MOVING OBJECT

(75) Inventors: Daniel Stapf, München (DE); Marcus Schreckenberg, Freising (DE)

(73) Assignee: Tomtec Imaging Systems GmbH (DE)

( * ) Notice: Subject to any disclaimer, the term of this patent is extended or adjusted under 35 U.S.C. 154(b) by 896 days.

(21) Appl. No.: 12/331,635

(22) Filed: Dec. 10, 2008

(65) Prior Publication Data
US 2010/0145197 A1    Jun. 10, 2010

(51) Int. Cl.
*A61B 8/00* (2006.01)
*G06K 9/00* (2006.01)

(52) U.S. Cl. .................. 600/443; 600/437; 382/128

(58) Field of Classification Search ............. None
See application file for complete search history.

(56) References Cited

U.S. PATENT DOCUMENTS

| | | | |
|---|---|---|---|
| 6,558,325 B1 * | 5/2003 | Pang et al. ............ | 600/443 |
| 6,980,844 B2 * | 12/2005 | Schoisswohl .......... | 600/407 |
| 7,731,660 B2 * | 6/2010 | Gardner et al. ........ | 600/437 |
| 7,854,702 B2 * | 12/2010 | Gardner et al. ........ | 600/450 |
| 7,981,035 B2 * | 7/2011 | Gardner et al. ........ | 600/437 |
| 2004/0064036 A1 * | 4/2004 | Mao et al. ............. | 600/413 |
| 2004/0066389 A1 * | 4/2004 | Skyba et al. ........... | 345/619 |
| 2005/0203416 A1 | 9/2005 | Angelsen et al. | |
| 2006/0241417 A1 | 10/2006 | Edwardsen et al. | |
| 2008/0027319 A1 * | 1/2008 | Gardner et al. ........ | 600/437 |
| 2008/0033294 A1 * | 2/2008 | Gardner et al. ........ | 600/437 |
| 2008/0199062 A1 | 8/2008 | Schummers et al. | |
| 2008/0205724 A1 | 8/2008 | Cocosco et al. | |

* cited by examiner

*Primary Examiner* — Long V. Le
*Assistant Examiner* — Angela M Hoffa
(74) *Attorney, Agent, or Firm* — Cantor Colburn LLP

(57) ABSTRACT

The invention relates to a device and method for generating a motion-corrected 3D image of a cyclically moving object by means of an ultrasound probe, comprising the steps of providing at least one 3D reference image of the object, the 3D reference image showing the object substantially at one particular phase in its cyclic movement; acquiring a set of sub-images of the object by sweeping the ultrasound probe over the moving object; registering at least two, preferably all, of the sub-images with the 3D reference image, thereby generating at least two motion-corrected sub-images; and reconstructing a motion-corrected 3D image from the motion-corrected sub-images. The invention is also directed to a corresponding device, computer program, and digital storage medium.

18 Claims, 5 Drawing Sheets

METHOD FOR GENERATING A MOTION-CORRECTED 3D IMAGE OF A CYCLICALLY MOVING OBJECT

Figure 1:
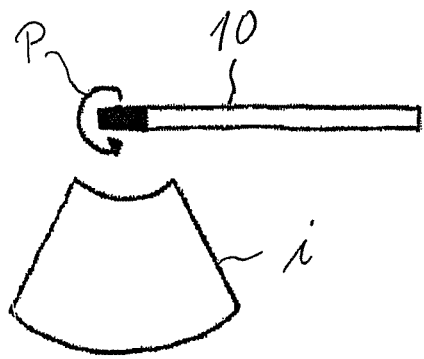

The present invention relates generally to the field of imaging, in particular medical imaging by means of ultrasound.

By means of a two-dimensional ultrasound probe, which may be swept to cover a certain volume, three-dimensional (3D) images of the human or animal body may be generated. For example, the ultrasonic probe is rotated about its own axis, ideally at constant rotational velocity. At regular intervals, essentially two-dimensional images are acquired at different angular positions. These two-dimensional (2D) images may afterwards be reconstructed to a three-dimensional image dataset. Such rotational ultrasonic probes or transducers are known for example from US 2005/0203416 A1, the contents of which are incorporated herewith by reference. A rotational ultrasonic transducer may be used in an intracardiac ultrasound catheter adapted for insertion into the heart. Further, transesophageal ultrasound probes for insertion into the esophagus and having an imaging element on the distal end of a rotating endoscope shaft are known for example from US 2006/241417.

The above-described method for generating 3D images yields good results when imaging static objects. When the image scene is dynamic, however, only a deformed image of the original scene can be obtained, because the imaged object moves while the ultrasound transducer sweeps over it. Such deformed 3D images are only of limited diagnostic use, since it is not possible to perform quantitative measurements such as distances, areas and volumes on such image datasets.

One particular application where it would be desirable to have a motion-corrected and thus undistorted 3D image, if possible in real-time, is ablation therapy of the heart. In this therapy, a catheter is inserted into the heart through a blood vessel. The catheter can be energized and is used to ablate certain areas of the heart tissue which are responsible for electric dysfunctions of the heart, for example atrial fibrillation. Evidently, the ablation catheter must be guided with high precision within the heart. Therefore, ablation therapy has been carried out in the past under X-ray control, i.e. by acquiring fluoroscopy images in real-time, while moving the catheter through the heart. Such X-ray monitoring has the disadvantage of high exposure to radiation both for the patient and especially the surgeon, who is not able to completely protect his hands from the radiation during his daily work.

Therefore, it is highly desirable that ablation therapy of the heart may be carried out under ultrasound control, rather than X-ray. In principle, intracardiac ultrasonic transducers are able to produce images of sufficient resolution and contrast to allow navigating an ablation catheter through the heart. However, for this application, it is highly desirable to produce 3D images of the heart in real-time.

Other devices allowing correct positioning of an ablation catheter within the heart are the products CARTO-Merge® or CARTO-Sound® of the company Biosense Webster. In this system, the catheter tip contains both a navigation sensor and an ultrasound phased array probe. The navigation sensor is based on a magnetic tracking system relying on an interaction between a magnetic field of specified direction and magnitude, positioned externally to the patient, and multiple small coils in the tip and on the shaft of the interventional catheter. While this system provides accurate position data, it also requires a time-intensive initialization of the scene. In addition, the position information is based on a reference system outside the patient, so that the initialization has to be repeated after any movement of the patient. Since ablation therapy not necessarily requires the patient to be completely anaesthetized, movements of the patient can easily happen during an ablation therapy. Furthermore, the geometry of the atrium may change during the therapy, for example as a consequence of infusions.

It is therefore an object of the invention to provide a method for generating a motion-corrected 3D image of a cyclically moving object. Ideally, this image should be available in real-time.

It is a further object of the invention to provide an imaging tool which may be used for navigating an ablation catheter through the heart without ionizing radiation.

These objects are accomplished by the method according to claim 1. Preferred embodiments of the invention are given in the dependent claims.

Before performing the image acquisitions, the ultrasound probe is preferably inserted into the body of a patient, for example into a cavity such as the esophagus or a blood vessel. Most preferably, the method of the invention is performed during intracardiac ultrasound, so that the ultrasound probe is mounted at the tip of an intracardiac catheter.

The ultrasound probe is adapted for acquiring so-called "subimages" of the cyclically moving object. A sub-image covers only a part of the 3D scan volume occupied by the object, so that several sub-images obtained by sweeping the ultrasound probe over the object can be reconstructed to one 3D image of the object. However, since the object will have moved while a sequence of sub-images has been acquired one after the other, such 3D image would be motion-distorted.

Preferably, such sub-image is a 2D image, such as a 2D image acquired with a 1D phased array ultrasound probe. By rotating such ultrasound probe, it is capable of acquiring a series of 2D images from a 3D scan volume in space. Since this type of 2D image is acquired by one ultrasound beam scanning the image in azimuthal direction while rotating the ultrasound probe, the 2D image will not necessarily be absolutely plane. The invention is applicable for planar and non-planar (curved) images. Furthermore, the invention is not limited to the reconstruction of a series of 2D image, but can also be applied on randomly shaped sub-images covering any subset of the 3D scan volume. Most preferred, the sub-image is a 2D image containing image data from a slice or plane of the 3D scan volume, wherein the plane may be planar or non-planar. Therefore, the terms "sub-image" and "2D image" are used interchangeably in the following. Whatever is described for the "2D images" may be generalised to the 3D "sub-images" mentioned in the claims.

The slice covered by one 2D image (i.e. a 2D image plane) may for example be fan-shaped due to diverging ultrasound beams, or rectangular. Sweeping the 2D image plane across a volume of space may be achieved by any means, wherein the following are only examples: Most preferred, sweeping is done by mechanical movement of the ultrasound probe, in particular by rotation of the ultrasound probe around an axis, as for example in intracardiac ultrasound catheters. The axis is preferably the longitudinal axis of the transducer, and the 2D image plane is either directed to the side of the rotational axis, or the axis lies within the 2D image plane. Alternatively, mechanical movement may be achieved by mounting the ultrasound probe on a wobbling structure so that the 2D image plane may be swept up and down, preferably in elevation direction. This will be called "panning" in this application. Thus, the ultrasound probe may be a rotational, panning or wobbling ultrasound probe. In another embodiment, sweeping of the 2D image plane is achieved not by mechanical means, but by means of a matrix-probe including e.g. a phased array of ultrasound transducers.

Generally, a "2D image" is a two-dimensional array of data points (dataset) containing image data corresponding to a certain image plane in space. The individual data points are called pixels. In the same way, a "3D image" is a three-dimensional array of data points (dataset) and a "4D image" is a four-dimensional array of data points, individual data points being called voxels. While a 3D image contains image data of a certain volume in space, a 4D image has the additional dimension of time. Thus, a "4D image" is a time series of 3D images.

The ultrasound probe is preferably adapted to record the position of each acquired 2D image, for example by noting the angular position of the 2D image plane. In case of a moveable or rotatable ultrasound probe, this can be done by monitoring the (angular) position of the probe.

The ultrasound probe may be part of an otherwise conventional ultrasound system, including a control unit for controlling acquisitions with the ultrasonic transducer, a processing unit for generally processing the acquired image data, a data storage component for storing image data, and usually a display device and a user input device, such as keyboard and/or computer mouse.

A cyclically moving object can be any object which performs a movement which repeats itself in time; preferably it is an organ of the human or animal body which moves periodically with respiration or with the heart beat, such as a blood vessel, an internal organ such as liver, spleen, lung, kidney etc. Most preferred, the cyclically moving object is the heart of a human or animal. One "phase" is one time point within the cycle of movement of the object.

The method of the invention requires at least one 3D reference image of the object. The 3D reference image can be obtained by any available means, but it should as far as possible show the object in one particular phase in its cyclic movement, i.e. the 3D reference image should not be distorted by movement. The 3D reference image can be generated by various medical imaging modalities, for example Computed Tomography (CT), Magnetic Resonance Imaging (MRI), 3D-Trans-Esophagal Ultrasound (3D-TEE) or 3D-Transthoracic Ultrasound (3D-TTE) etc. Preferably, the 3D reference image is acquired with the same ultrasound probe as the 2D images. The 3D reference image may be acquired over several cycles of movement, for example by acquiring at least one 2D image of one particular image plane during one cycle, and then moving the image plane of the ultrasound probe incrementally to the next position, to acquire at least one 2D image during the next cycle. Such acquisition can be triggered by an ECG (Electrocardiogram) or a respiration trigger system in order to ensure that each 2D image is taken at the same phase of the cycle of movement. Such 2D images can then be reconstructed to obtain the 3D reference image. The 3D reference image is preferably acquired at the beginning of a diagnostic or therapeutic session (intervention).

Further, a set of sub-images or 2D images of the object is acquired preferably by sweeping the ultrasound probe over the moving object while acquiring a series of 2D images. Such sweep is also called "fast sweep" and is preferably performed during an actual intervention in order to obtain real-time images of the object. The fast sweep is preferably acquired within the same diagnostic or therapeutic session as the 3D reference image, most preferred with the ultrasound probe at the same position within the body of the patient than during acquisition of the 3D reference image. The series of 2D images can be acquired at regular or irregular time intervals.

Such fast sweep might for example entail sweeping the image plane of the ultrasound probe over a sector of 40-120°, whereby 2D images are acquired every 1°-5°. The speed of sweeping will depend on the maximum available image acquisition rate, which may be somewhere between 25-400 images per second. The acquisition of the "fast sweep" will preferably take less than one movement cycle, for example 0.05-1 movement cycles or 20-500 ms. In other less preferred embodiments, the fast sweep may take about 1-3 movement cycles or heart beats.

In step c), at least two, preferably all, of the 2D images acquired with said fast sweep are registered with the 3D reference image, to thereby generate at least two motion-corrected 2D images. In other words, each 2D image is motion-corrected by registering it with the 3D reference image, which shows the object in one particular time phase in its cyclic movement. The 2D image of the real-time fast sweep may show the object at a completely different time phase and therefore rather distorted in comparison with the 3D reference image.

This registration is preferably carried out with each, or at least most, of the 2D images acquired during the fast sweep.

Registration is a computerized method by which two images showing the same object, but in different positions or poses are overlaid with one another. Thus, registration is a mapping or transformation of each pixel/voxel in one image to the corresponding pixel/voxel in the other image, i.e. the one showing approximately the same point in space. Registration algorithms are well-known in medical imaging, as they are often required to compare images of the same patient acquired with different imaging modalities (e.g. ultrasound, MRI, CT or X-ray) with one another. For the present invention, a non-rigid registration algorithm is preferably used, i.e. a registration algorithm which allows for relatively large distortion of one image when computing the transformation into the other.

Suitable non-rigid registration algorithms are known in the art, and are disclosed for example in Jan Modersitzki: "Numerical Methods for Image Registration", Oxford University Press, 2004; Jan Kybic, Michael Unser: "Fast Parametric Elastic Image Registration", IEEE Transactions on Image Processing, Vol. 12, No. 11, November 2003 as well as D. Rueckert, L. I. Sonoda, D. L. Hill, M. O. Leach, D. J. Hawkes: "Nonrigid registration using free-form deformations: Application to breast MR images", IEEE Transactions on Medical Imaging 18(8), pp. 712-721, 1999 and J. B. A. Maintz, M. A. Viergever: "A survey of medical image registration", Oxford University Press, Medical Image Analysis 2(1), S. 1-36, 1998.

Finally, the 2D motion-corrected images are reconstructed to form a motion-correct 3D image. This may be performed simply by putting all motion-corrected 2D images together, each at its correct position, in a 3D dataset. Optionally, interpolation may be performed to fill up those voxels not covered by any of the motion-corrected 2D images. However, care must be taken that the reconstruction is as fast as possible, since the motion-corrected 3D image is preferably to be used immediately, preferably in real-time, during a diagnostic or therapeutic intervention.

Preferably, steps b) to d) as defined in claim 1 are consecutively repeated over a certain time period, in which real-time motion-corrected 3D images are required. This might be during at least part of an interventional procedure. During this time period, one set of 2D images after the other is acquired by a fast sweep, and the registration and reconstruction of one set of 2D images is preferably completed by the time the next set of 2D images is acquired. This would be called "real-time". For example, 0.1 to 10 fast sweeps may be completed per cycle of movement.

Such series of motion-corrected 3D images can advantageously be used to navigate a catheter in the human heart, in particular an ablation catheter. Such catheters may be clad with a material which ensures that the ablation catheter is visible on ultrasound images.

Preferably, the 3D reference image is acquired by the following method: The ultrasonic transducer is moved only once every cycle at a fixed time point within the cycle, by a predetermined increment, for example 1-3°. While the ultrasonic probe is in a fixed position, a series of 2D images is acquired during one cycle, while the movement is monitored by means of ECG or the like. Then, the probe is moved, e.g. rotated, by the predetermined increment. This is repeated until the probe has been moved to cover a desired sector in space. Finally, all 2D images acquired during the same time phase of the cyclic movement, but while the probe was in different positions, are combined to one 3D reference image. Since it is possible to reconstruct 3D reference images for each phase of the cycle, these 3D volumes may be combined to a 4D reference image, in which time is the fourth dimension. This process allows the acquisition of an undistorted 4D reference image suitable for quantitative analysis. However, since one needs many cycles of movement to create such image, the acquisition time is about 1-5 minutes, which is too long for navigating a catheter. However, it is no problem to spend these few minutes at the beginning of an interventional procedure.

Optionally, the 2D images acquired during the same time phase of the cyclic movement, but with the probe in different positions, are registered with one another by means of a rigid body registration algorithm, before they are combined to one 3D reference image. In particular, 2D images which are adjacent to one another in space may be registered with one another by a rigid 2D-2D registration in order to reduce blurring in case the ultrasound probe has changed its absolute position (not only its rotational position) in relation to the object between different cycles.

Furthermore, interpolation may be used when reconstructing the 3D reference image(s), in order to provide data for those voxels not covered by any of the 2D images acquired during the same time phase of the cyclic movement. Especially in the outer regions, the spacing between the 2D image slices may be larger than desired.

There are several ways in which a registration of the set of 2D images with the 3D reference image may be performed. Generally, it is preferred that the transformation matrix, necessary for the mapping of each 2D image onto the 3D reference image is not calculated afresh in each iteration of steps b) to d). Rather, it is preferred that a suitable 3D transformation matrix (in the following "3D transform") is computed only once or a few times, and used to motion-correct many sets of 2D images acquired during consecutive fast sweeps.

According to the most preferred embodiment, the 3D transformation matrix is updated from time to time. For example, a new 3D transform may be calculated in regular intervals, for example 2-3 minutes. According to the most preferred embodiment, each or every N motion-corrected 3D image is compared with the 3D reference image. In such comparison, the images are preferably overlaid with one another and a matching coefficient is calculated. If such matching coefficient shows that the motion-corrected 3D image does not conform well with the 3D reference image, the method concludes that the object must have moved since the last 3D transform was calculated, and therefore a new 3D transform is calculated, preferably according to the second embodiment of the registration described below.

Generally, a 2D-2D registration could be used, but only if the object does not move out of the 2D image plane during its cyclic movement. In the general case, a 3D-3D transformation matrix will be used to register each 2D image acquired with a fast sweep with the 3D reference image. It is necessary to know the position of each 2D image within space to apply a 3D-3D transform. It is also possible to put the set of 2D images acquired during one fast sweep (step b) together to one motion-distorted 3D image data set, which is then subjected to a 3D-3D transformation to directly generate a motion-corrected 3D image.

Two particular embodiments of the registration are preferred: The first embodiment according to claim 4 requires that the 3D reference image is part of a 4D reference image comprising several 3D images showing the object at different time phases in its cyclic movement. One of these 3D images is selected as the 3D reference image. Preferably, it shows the object in a suitable time phase, e.g. end diastole. For example, the 4D reference image may be acquired by means of the method described above. Once during the method of the invention, preferably before the first fast sweep of step b), a non-rigid 3D transform between each 3D image in the 4D reference image and the 3D reference image is computed, to thereby generate several 3D transforms corresponding to different time phases in the cyclic movement. A "3D transform" stands for a mapping between one 3D image and another 3D image. In other words: A 4D reference image comprises several 3D images, each acquired during a different time phase. One of the time phases is selected as reference phase. Next, a 3D transform is computed from each of the non-reference 3D images into the 3D reference image. For each 2D image to be registered during the registration step, one selects that 3D image of the 4D reference image which corresponds to the time phase in which the 2D image was acquired, and uses the associated 3D transform to transform this 2D image into a motion-corrected 2D image. Thus, each 2D image obtained with one fast sweep might be registered using a different 3D transform, since each 2D image is acquired during a different time phase. From these motion-corrected 2D images, a reverse deformed 3D image may be reconstructed which matches the global geometry of the 3D reference image, but still contains the local real-time detail.

This first embodiment requires that the time phase in which each 2D image was acquired is known, so that it can be associated with the corresponding 3D transform. Suitable mechanisms for associating the time phase of the cyclic movement are described below. However, it is not necessary to trigger the fast sweep to always start at the same time phase of the cyclic movement.

According to a second embodiment, a non-rigid 3D transform is computed between the set of 2D images acquired in the first fast sweep and the 3D reference image. In this case, this 3D transform is then used to register the 2D images acquired during the following fast sweeps into motion-corrected 2D images. This embodiment requires that the fast sweep is always triggered to start at the same time phase of the cyclic movement.

As disadvantage of this second embodiment is that the first fast sweep cannot be motion-corrected since it is used to calculate a 3D transform to be used for the later registration. Therefore, the following variant of the second embodiment is more preferred: A 4D reference image is acquired according to the preferred method described above. From the 4D reference image, a set of 2D images which might be acquired during one fast sweep is extracted. This can be done by selecting a set of 2D images acquired at consecutive angular positions and time phases from the raw image data, or by extracting the corresponding data from the 4D image dataset. This set of 2D images will be called "pseudo fast sweep" in the following. Next, a 3D transform is computed between the set of 2D images of the pseudo fast sweep and the 3D reference image. This 3D transform is used in the following for motion-correction of 2D images acquired in the following fast sweeps. Again, this method requires that each fast sweep is started at the same time phase. This variant has the advantage that the registration will be more exact, and that already the first fast sweep can be motion-corrected.

In principle, the 3D transformation matrix has only to be calculated once. However, it might be advantageous to repeat the computation of a 3D transform with a set of 2D images acquired in a later iteration of the fast sweep, in order to compensate for possible patient movement in the meantime.

According to another less preferred embodiment of the registration step, a 2D-2D registration algorithm may be used, preferably in applications where the object will not move out of the image plane, for example in case of a blood vessel, which expands and contracts, but does not change its position with the heart beat. In this embodiment, each 2D image acquired with a fast sweep is registered with a slice of a 3D reference image corresponding to the 2D image, to thereby generate a motion-corrected 2D image. As described above, it is possible to calculate a 2D-2D transformation matrix for each possible image slice of the 3D reference image once, either from the first fast sweep or from a 4D reference image. This 2D-2D transform may be used for the following fast sweeps.

To carry out the registration step, in particular according to the first embodiment above it is advantageous to associate each 2D image of the set of 2D images acquired during one fast sweep with the corresponding time phase of the cyclic movement, in which it was acquired. This can be achieved by several means:

First of all, the time phase may be derived from the image content, i.e. the state of distortion of the heart allows to deduce the respective phase during the heart cycle at least approximately. Secondly, the cyclic movement may be monitored during the ultrasound acquisitions. This can be done for example with a second ultrasound probe, or possibly by acoustic monitoring. In the case of the beating heart, the sound of the heart beat may be used to gauge the time for each heart beat.

Furthermore, in the case of the beating heart, the time phase for each 2D image acquired during a fast sweep may be obtained by taking an electrocardiogram (ECG). The ECG electrodes are attached to the patient's chest and the electric signals allow detecting for example the R-wave. In case of respiratory movement, an elastic belt may be wound round the patient's chest in order to monitor the breathing motion.

Such acoustic, ultrasound, ECG or breathing monitoring of the time phase may preferably be used to trigger at least the sweeping acquisition ("Fast sweep"), so that it is always started at the same, suitable phase within the cycle of movement. For example, the fast-sweep can be timed to take place during the period of the heart cycle with least movement, for example during the diastole.

Preferably, the fast sweep is synchronized with the cyclic movement, so that the angular position of each 2D image and the time phase in which this 2D image was acquired, are always the same for each fast sweep. If this is the case, it is not necessary to monitor the time phase during each cyclic movement. This is achieved by triggering, preferably ECG triggering. Alternatively, if the heart of a patient is forced into a certain cycle during an intervention by means of suitable external simulation, the fast sweeps may be triggered by the external stimulus.

Moreover, the above-described acoustic, ultrasound, ECG or breathing monitoring of the time phase may also be used to trigger the acquisition of the 3D reference image.

The invention is also directed to a computer program comprising instructions to cause a processor to carry out the above-described steps. The processor can be part of an otherwise conventional ultrasound imaging system including an ultrasound probe with which the respective images are acquired. The computer programme includes the registering algorithm and the reconstruction algorithm of steps c) and d). All preferred features of the claimed method can also be comprised in the computer program.

Furthermore, the invention is directed to a digital storage medium on which the computer program is stored.

Finally, the invention can be embodied in a device for generating a motion-corrected 3D image of a cyclically moving object. The device comprises an ultrasound probe as described above. Furthermore, the device includes a data storage component such as a hard disc adapted for storing image data acquired by the ultrasound probe.

Furthermore, the device comprises a control unit adapted to control the ultrasound probe to perform the above-described image acquisitions. Further, the device includes a processing unit adapted to perform the above-described registration and reconstruction steps. Preferably, the processing unit is adapted to perform each of the above-described preferred method steps. The device may also include a conventional ECG device.

Figure 3:
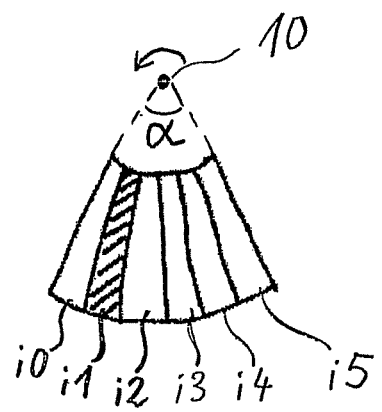
Figure 2:
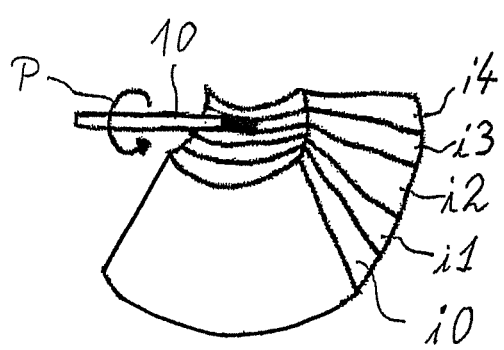
Figure 4:
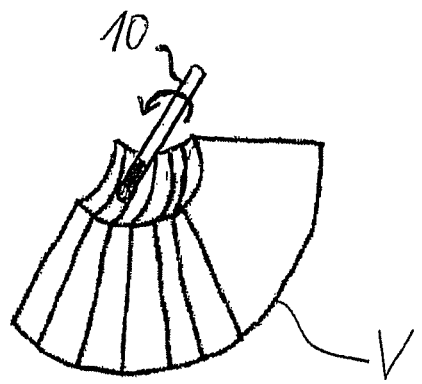
Figure 5:
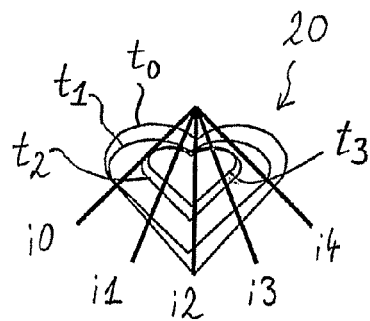
Figure 6:
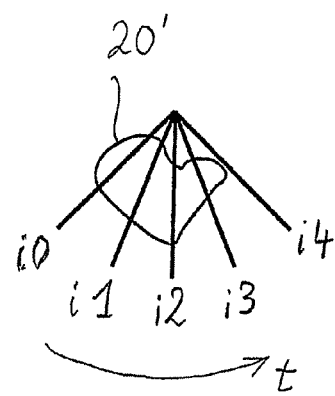
Figure 7:
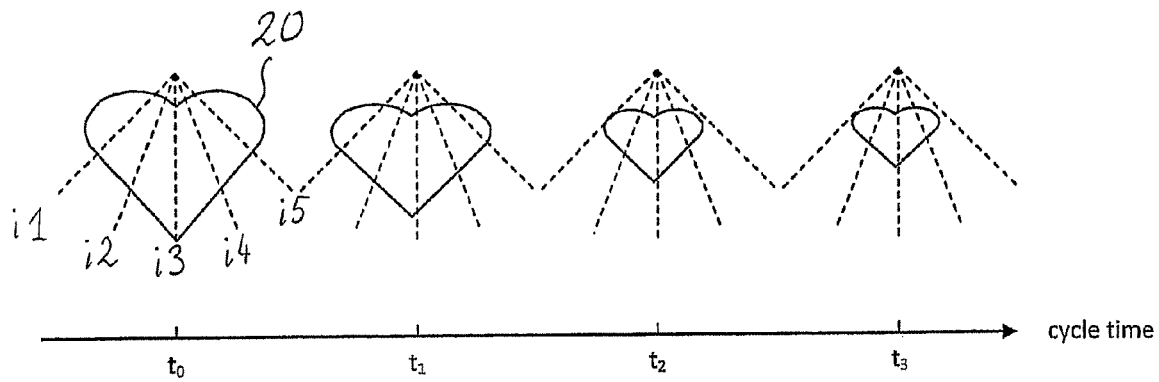
Figure 8:
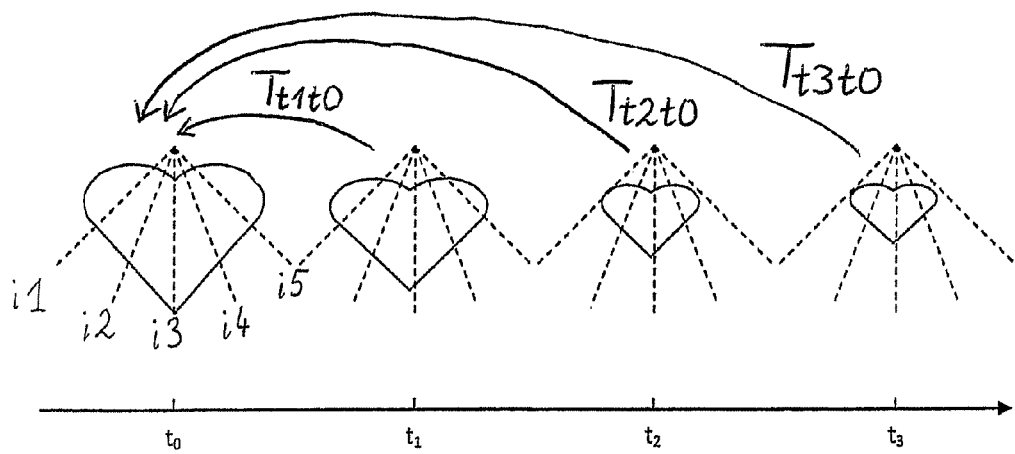
Figure 9:
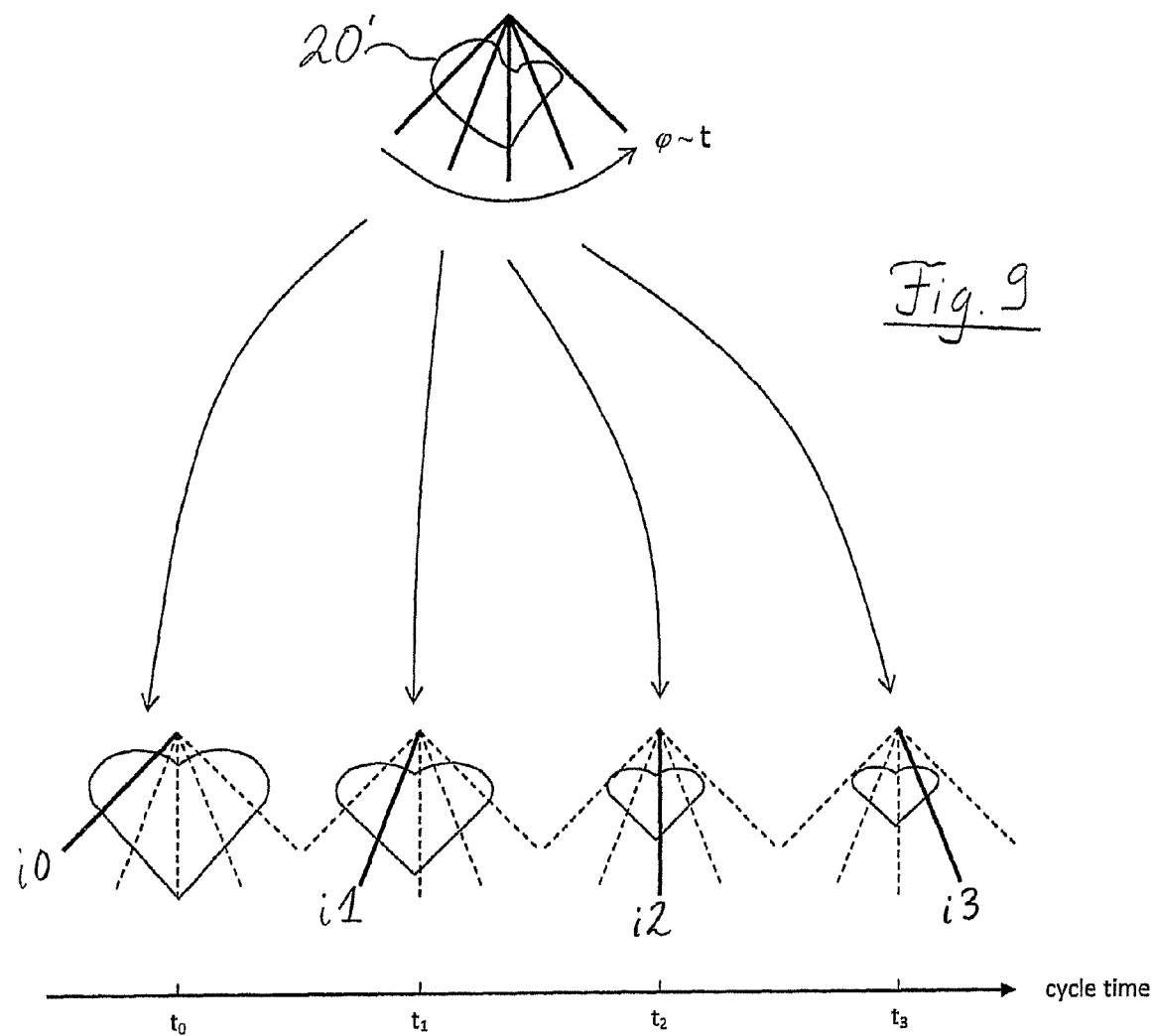
Figure 10:
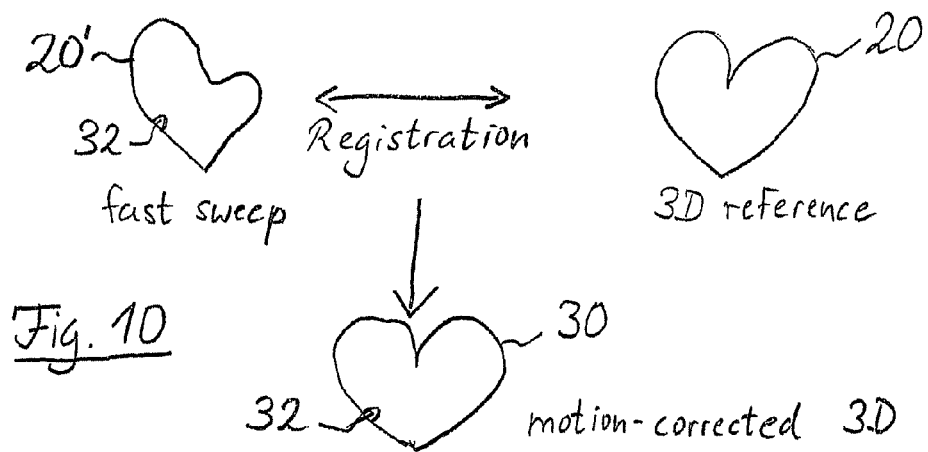
Figure 11:
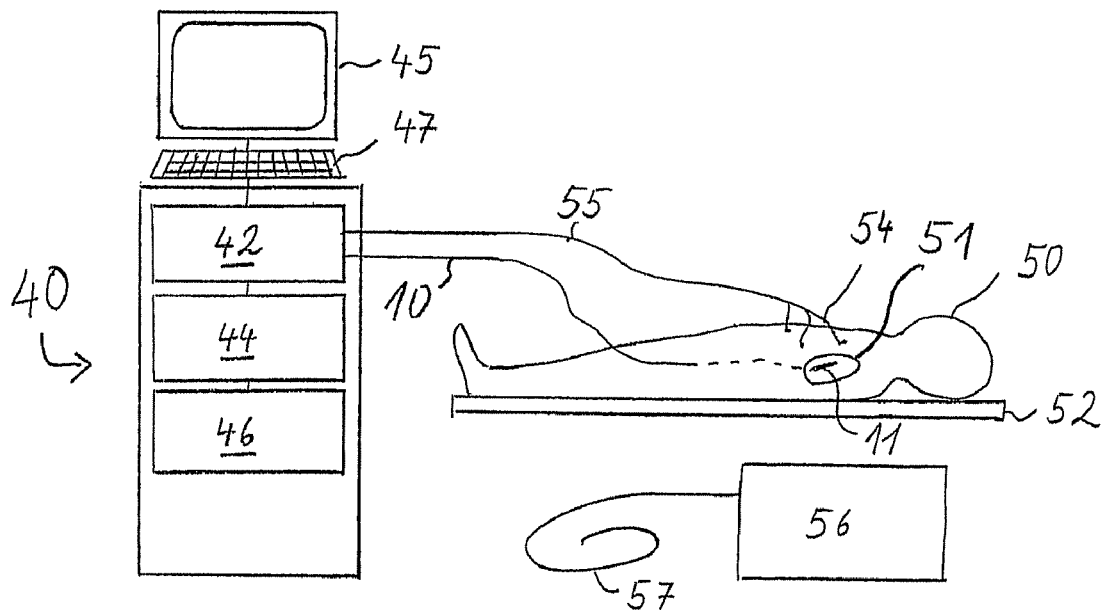
Figure 12:
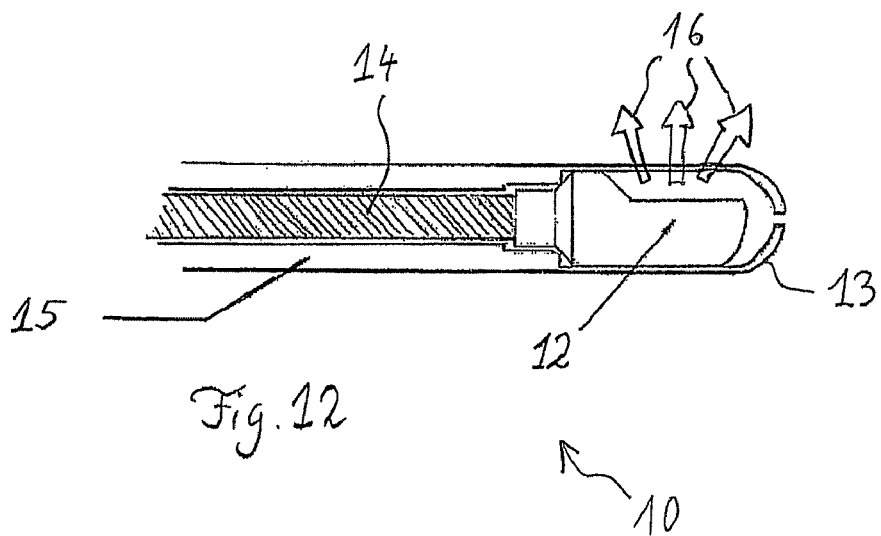
Figure 13:
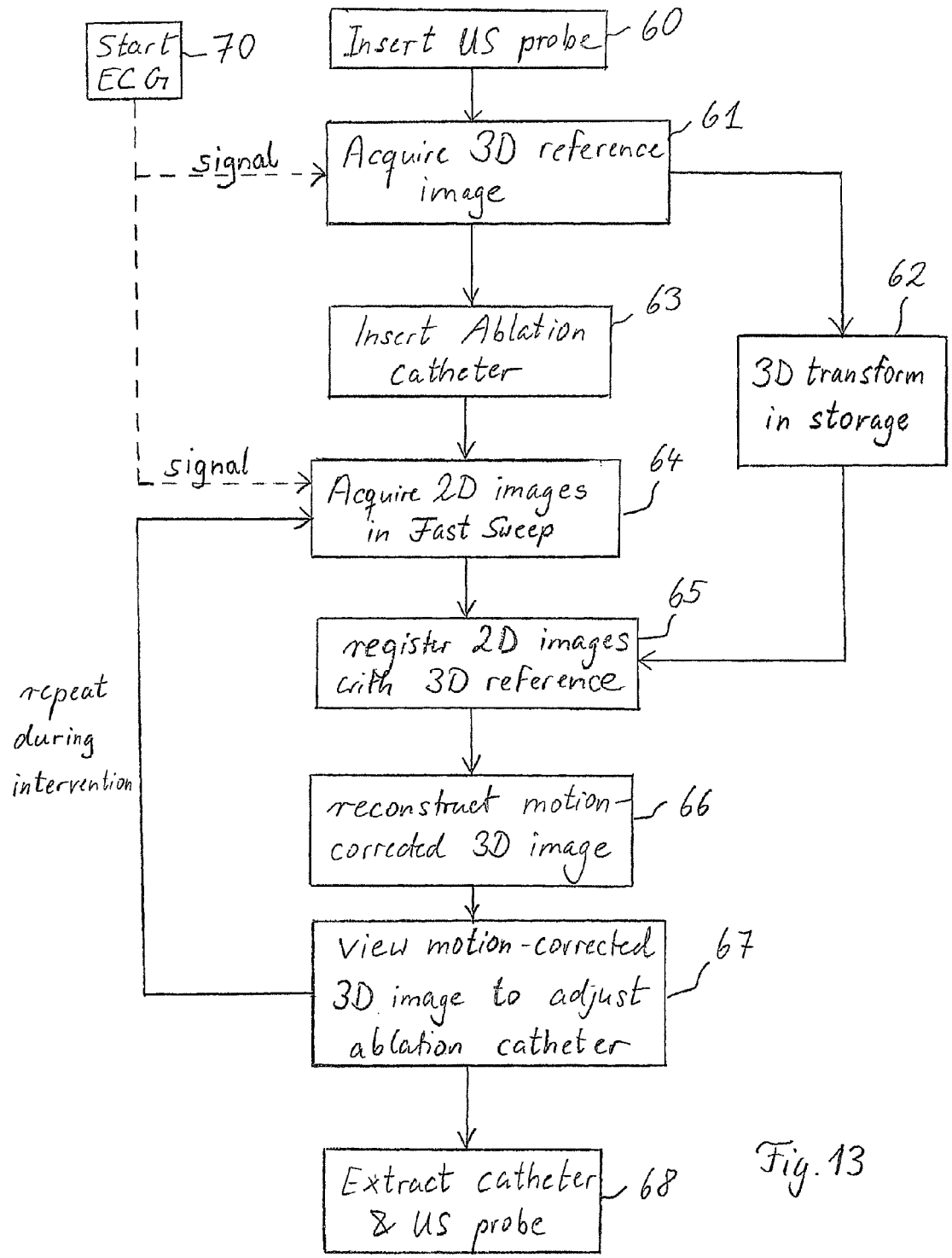

Preferred embodiments of the invention will now be described with reference to the accompanying figures, which show:

FIG. 1 A schematic side view of an ultrasound catheter and its field of view;

FIG. 2 A perspective view of several 2D images acquired with the ultrasound catheter of FIG. 1;

FIG. 3 A front view of the set of 2D images shown in FIG. 2;

FIG. 4 A front perspective view of the set of 2D images acquired by rotating the ultrasound catheter of FIG. 1;

FIG. 5 A schematic view of a set of 2D images of a moving object acquired with a fast sweep;

FIG. 6 A schematic view of the object, as reconstructed from the set of 2D images in FIG. 5;

FIG. 7 A schematic illustration of a 4D reference image;

FIG. 8 A schematic illustration of the computation of 3D transforms between the 3D images contained in the 4D reference image of FIG. 7;

FIG. 9 A schematic illustration of the registration of each of the 2D images of the set of 2D images in FIG. 5 with the 3D reference image;

FIG. 10 A schematic representation of the registration step between the 2D images of a fast sweep and the 3D reference image;

FIG. 11 A schematic representation of a device according to an embodiment of the invention;

FIG. 12 A cross-sectional view of an ultrasound catheter;

FIG. 13 A flowchart of an embodiment of the claimed method.

FIGS. 1-4 demonstrate the geometry of the 2D images which can be acquired in a preferred embodiment of the invention with a rotational ultrasound probe, such as an ultrasound catheter as depicted in FIG. 12. According to FIG. 12, an ultrasound catheter 10 comprises a drive cable 14 enclosed in a sheath 15. At the tip of the catheter, the transducer 12 is mounted rotatably in a cover 13. The transducer 12 emits ultrasound beams, and receives the reflected echoes. The ultrasonic beams are emitted in the directions of arrows 16, e.g. to the side.

Thus, the ultrasound probe 10 will be able to acquire an approximately fan-shaped 2D image slice 1, as shown in FIG. 1. By rotating the ultrasound (US) catheter around its own axis, as indicated by arrow P, a stack or set of 2D images i0, i1, i2, i3, i4 can be acquired one after the other, as shown in FIG. 2. In practice, the set of 2D images will comprise more than 5, for example 20 to 400 2D images.

The same set of 2D images is shown in FIG. 3 in front view. As can be imagined, the 2D images thus acquired may be reconstructed to a 3D image dataset. The image slice shown hatched indicates that this complete volume can be interpolated from the neighbouring image slices. The 2D image slices i0, i1, i2, i3, ... in FIG. 3 altogether cover an angle α of about 60°-120° in elevation direction.

FIG. 4 shows the 3D image volume V reconstructed from the 2D images i0 ... i5 of FIG. 3 in perspective view.

FIG. 5 shows a schematic view similar to FIG. 3, i.e. a number of 2D image slices i0 ... i4, which are acquired one after the other by sweeping the image plane of the ultrasound probe 10 over an angle of for example 90° in for example 1 sec. During this time, e.g. about 20-400, preferably as many as possible, 2D images per second are acquired by the ultrasound probe. The object 20 representing the heart is shown in FIG. 5 at different time phases t0, t1, t2, t3, which correspond to the time phases during which the 2D images i0, i1, i2 and i3, respectively, are acquired during the fast sweep. Since the heart 20 contracts while the images i0 ... i4 are taken one after the other, the 3D image obtained by combining those 2D images will not show the object 20 as a perfectly shaped heart. Instead, it will show an object 20' as shown in FIG. 6. Generally, the heart 20' is shown expanded on the left, and contracted on the right. It is an object of the invention to acquire 3D image sets of the heart with fast imaging methods, which do not show this kind of deformation.

FIG. 7 illustrates the acquisition of a 4D reference image. The image plane (depicted by dashed lines) will remain for one heart cycle in the same angular position. Therefore, a 3D image can be constructed for each time phase. The distance in time between consecutive 3D images corresponds to the rate of acquisition of the 2D images during acquisition. Thereby, it is possible to reconstruct a non-distorted image of the heart 20 during each time phase t0 and t1, t2 and t3.

From this 4D image data set, one phase within the cycle may be chosen to serve as 3D reference image, for example the 3D image acquired at t0.

As illustrated by FIG. 8, each of the other 3D images corresponding to time phases t1, t2 and t3 may be registered with the 3D reference volume by non-rigid registration. These 3D transforms $T_{t1t0}$, $T_{t2t0}$, $T_{t3t0}$ allow to assign to each voxel within the 3D images corresponding to time phases t1, t2, t3, the corresponding position in the 3D reference image at time phase t0.

FIG. 9 illustrates the relationship between each of the 2D images i0 ... i4 acquired during a fast sweep, to the corresponding image slices of the 4D reference image. As can be seen, each angular position corresponds to a different time phase, therefore a different 2D or 3D transform has to be used. Thus, if each of the 2D images i0 ... i4 of the fast sweep is mapped with the corresponding transformation $T_{tnt0}$ into the 3D image volume, one obtains the overall geometry of the 3D reference image at time phase t0.

The overall mechanism is illustrated in a different way in FIG. 10. According to this figure, the distorted object 20' acquired with the fast sweep in 3D is registered with the undistorted 3D reference, showing the object 20 at one particular time phase. The thus acquired motion-corrected 3D image 30 contains real-time image details 32 from the fast sweep, but in the overall geometry of the 3D reference image.

FIG. 11 schematically shows a device with which the invention may be carried out. Ultrasound apparatus 40 is configured in known manner with a control unit 42 which controls the operation of an ultrasound catheter 10. The ultrasound catheter may be inserted via a large vein into the heart 51 of a patient 50, for example such that the tip 11 of the catheter is positioned in an atrium. Patient 50 is positioned on an operating table 52. In order to trigger the acquisitions performed with the ultrasound catheter 10, an ECG signal can also be acquired from the patient 50 by means of ECG electrodes 54. These are connected with the control unit 42 via cables 55.

The ultrasound device 40 further includes a processor 44 suitable for performing fast registrations and reconstruction of 2D images into 3D images, and a data storage 46. Furthermore, the ultrasound device may include a display screen 45 and a keyboard 47 and possibly mouse to allow manipulation by a user, such as the surgeon. Those components are all interconnected with one another by suitable cables.

FIG. 11 further shows an ablation catheter 57 and the corresponding equipment 56. In an interventional ablation therapy, the catheter 57 may be inserted into the patient's heart 51 to selectively ablate cardiac tissue. Such intervention may be monitored by means of the ultrasound catheter 10.

Finally, a flowchart of an embodiment of the method according to the invention is shown in FIG. 13. At 60, the ultrasound (US) probe is inserted into the heart. Optionally, an ECG measurement 70 is started at around the same time and the ECG signal will continuously be acquired during the intervention.

The ECG signal can be used in step 61 for the acquisition of the 3D reference image of the moving object. Before or afterwards, an ablation catheter may also be inserted into the heart in step 63.

From the 3D reference image 61, a 3D transform 62 is computed and kept in storage for later use during the registration step. The 3D transform can be computed between different 3D images of a 4D reference image, or between the 3D reference image and the first set of 2D images from a fast sweep, or between the 3D reference image and the set of 2D images from a pseudo fast sweep, as described above. Then, the fast sweeps of the object are started in step 64. For example once every cycle, the transducer 12 in the catheter tip 10 is swept over the desired field of view, wherein a series i1 ... iN of N 2D images is acquired.

In step 65, each of these 2D images is registered with the 3D reference image 61, preferably by using the 3D transform 62. In step 66, the registered, i.e. motion-corrected 2D images are put together to construct a motion-corrected 3D image. In step 67, this motion-corrected 3D image is displayed for example on screen 45 and used to position the ablation catheter 57. Steps 64, 65, 66 and 67 are repeated as fast as possible, wherein step 64 is started again even before step 67 is finished. It is envisaged that the processing time for each of these repeat cycles will take less time than the acquisition time for one fast sweep, so that the motion-corrected 3D images can be displayed in real-time. For example, a new motion-corrected 3D image will be generated for every cycle or heart beat, e.g. every 0.2-2 sec.

Thus, the method of the invention allows real-time acquisition of motion-corrected 3D images.

About every $10^{th}$ to $500^{th}$ motion-corrected 3D image is compared with the 3D reference image to find out whether the 3D transform 62 is still adequate. If not, a new 3D transform is calculated between the 2D images acquired in a recent fast sweep 64, and the 3D reference image as new 3D transform 62, and used in subsequent registration steps 65.

Finally, in step 68 both the US probe and the ablation catheter are extracted, after the ablation therapy is finished.

Having now fully described the invention, it will be apparent to one of ordinary skill in the art that many changes and modifications can be made without departing from the spirit or scope of the invention as herein described.

The invention claimed is:

1. A method for generating a motion-corrected 3D image of a cyclically moving object by means of an ultrasound probe, comprising the following steps:
    a) providing at least one 3D reference image of the object, wherein the 3D reference image covers a 3D scan volume and shows the object substantially at one phase in the cyclic movement of said object;
    b) acquiring a set of at least two sub-images of the cyclically moving object with the ultrasound probe, each of the sub-images covering a 3D subset of the 3D scan volume;
    c) registering at least two of the set of sub-images acquired in step b) with the 3D reference image by using of a non-rigid transformation, thereby generating at least two motion-corrected sub-images;
    d) reconstructing a motion-corrected 3D image from the motion-corrected sub-images; and
    e) displaying the reconstructed motion-corrected 3D image.

2. The method of claim 1, wherein the set of at least two sub-images is acquired by sweeping the ultrasound probe over the moving object while acquiring a time sequence of sub-images in a first sweeping acquisition.

3. The method of claim 2, wherein steps b) to d) are consecutively iterated over a time period, and wherein the method comprises:
    computing a non-rigid 3D transformation between the set of sub-images acquired in the first sweeping acquisition, and the 3D reference image,
    determining the time phase in which the sub-image was acquired; and
    using the 3D transformation to transform at least two of the sub-images acquired during a following sweeping acquisition into motion-corrected sub-images,
    wherein each sweeping acquisition is started at the same phase in said cyclic movement.

4. The method of claim 3, wherein a new 3D transformation is computed between a set of sub-images in a later iteration of the sweeping acquisition and the 3D reference image, and wherein said new 3D transformation is used to transform at least two of the sub-images acquired during a following sweeping acquisition into motion-corrected 2D images.

5. The method of claim 1, wherein steps b) to d) are consecutively iterated over a time period, wherein in each iteration, a new motion-corrected 3D image is reconstructed from the newly acquired sub-images.

6. The method of claim 1, wherein the registration step c) is performed using a non-rigid 3D-3D or 2D-2D registration algorithm.

7. The method of claim 1, wherein the 3D reference image is part of a 4D reference image comprising several 3D images showing the object at different time phases in said cyclic movement, and wherein the method comprises:
    computing a non-rigid 3D transformation between each non-reference 3D image in the 4D reference image and the 3D reference image, to thereby generate several 3D transformations corresponding to different time phases in a cyclic movement;
    for each sub-image to be registered during registration step c), determining the time phase in which the sub-image was acquired, selecting the 3D image of the 4D reference image which corresponds to the time phase in which the sub-image was acquired, and using the associated 3D transformation to transform said sub-image into a motion-corrected sub-image.

8. The method of claim 1, wherein the moving object is the heart of a human or animal.

9. The method of claim 8 further including the step of navigating a catheter in the heart.

10. The method of claim 1, wherein the sweeping acquisition in step (b) is timed so that one sweeping acquisition is carried out during one cycle of movement of the object.

11. The method of claim 1, wherein the ultrasound probe is a 2D matrix probe.

12. The method of claim 1, wherein the 3D reference is obtained by
    acquiring a series of sub-images during one cycle of the cyclic movement while the ultrasound probe is in a fixed position;
    rotating the image plane of the ultrasound probe by a predetermined increment;
    repeating the two previous steps, until the ultrasound probe has been moved to cover a required sector in space;
    determining the time phase in which each sub-image was acquired; and
    combining all sub-images acquired during the same time phase of the cyclic movement to one 3D reference image.

13. The method of claim 12, wherein the 3D reference images corresponding to different time phases of the cyclic movement are combined to one 4D reference image, and wherein for each sub-image to be registered in step 1), the 3D reference image is selected which corresponds to the time phase in which the sub-image was acquired.

14. The method of claim 13, wherein at least two of the sub-images acquired during the same time phase of the cyclic movement are registered with one another by means of a rigid body registration algorithm, before they are combined to one 3D reference image.

15. The method of claim 1, wherein the voxels not covered by any of the motion-corrected sub-images are interpolated during the reconstruction of the motion-corrected 3D image in step d).

16. A non-transitory computer program for generating a motion-corrected 3D image of a cyclically moving object, said computer program comprising instructions to cause a processor to carry out the following steps when the program is executed on the processor:
    a) accessing at least one 3D reference image of the object, the 3D reference image showing the object at one particular phase in the cyclic movement of said object;
    b) accessing a set of sub-images of the object acquired by sweeping an ultrasound probe over the moving object;
    c) registering at least two of the sub-images accessed in step b) with the 3D reference image by using of a non-rigid transformation, thereby generating at least two motion-corrected sub-images;
    d) reconstructing a motion-corrected 3D image form the motion-corrected sub-images; and
    displaying the reconstructed motion-corrected 3D image.

17. A non-transitory digital storage medium containing program code for generating a motion-corrected 3D image of a cyclically moving object, said program code comprising instruction to cause a processor to carry out the following steps:
   a) accessing at least one 3D reference image of the object, the 3D reference image showing the object at one particular phase in the cyclic movement of said object;
   b) accessing a set of sub-images of the object acquired by sweeping an ultrasound probe over the moving object;
   c) registering at least two of the sub-images accessed in step b) with the 3D reference image by using of a non-rigid transformation, thereby generating at least two motion-corrected sub-images;
   d) reconstructing a motion-corrected 3D image from the motion-corrected sub-images; and
   e) displaying the reconstructed motion-corrected 3D image.

18. A device for generating a motion-corrected 3D image of a cyclically moving object, the 3D image covering at least a part of a 3D scan volume, comprising:
   an ultrasound probe configured to acquire a set of sub-images, each of the sub-images covering a 3D subset of the 3D scan volume;
   a data storage component configured to store image data acquired by the ultrasound probe, and further configured to store at least one 3D reference image of the object, the 3D reference image showing the object substantially at one phase in its cyclic movement; and
   a control unit configured to control the ultrasound probe to acquire a set of sub-images of the object by sweeping the ultrasound probe over the moving object;
   a processing unit configured to register at least two of the sub-images with the 3D reference image by using a non-rigid transformation, thereby generating at least two motion-corrected sub-images; and further configured to reconstruct a motion-corrected 3D image from the motion-corrected sub-images; and
   a display unit configured to display the reconstructed motion-corrected 3D image.

* * * * *